United States Patent [19]

Schulte-Elte et al.

[11] Patent Number: 4,480,107
[45] Date of Patent: Oct. 30, 1984

[54] PYRANIC DERIVATIVES USEFUL AS INTERMEDIATES IN MAKING MUSCONE

[75] Inventors: Karl H. Schulte-Elte, Onex/Ge; Joseph J. Becker; Walter Schenk, both of Geneva, all of Switzerland

[73] Assignee: Firmenich SA, Switzerland

[21] Appl. No.: 323,578

[22] Filed: Nov. 20, 1981

Related U.S. Application Data

[62] Division of Ser. No. 183,722, Sep. 3, 1980, Pat. No. 4,335,262.

[30] Foreign Application Priority Data

Sep. 13, 1979 [CH] Switzerland .......................... 8293/79

[51] Int. Cl.³ .......................................... C07D 313/00
[52] U.S. Cl. .................................................... 549/355
[58] Field of Search .............................. 549/355, 397

[56] References Cited

PUBLICATIONS

Schulte-Elte et al., Hzlv. Chim. Acta, 1979, 62 (8), 2673-2680.

Primary Examiner—Nicky Chan
Attorney, Agent, or Firm—Pennie & Edmonds

[57] ABSTRACT

Process for the preparation of muscone starting from pyranic derivatives by treatments thereof with hydrogen in an inert organic solvent and in the presence of a noble metal catalyst. Compounds of formula

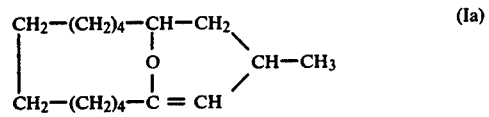

(Ia)

and process for its preparation via dehydrogenation and dehydration of corresponding diol. Process for the preparation of unsaturated macrocyclic ketones of formula

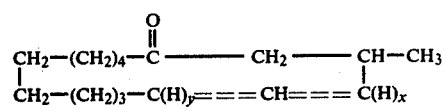

wherein the dotted lines stand for a single or a double bond
wherein
  $x=1$ and $y=2$, or
  $x=2$ and $y=1$, starting from compound (Ia) via acidic treatment.

1 Claim, No Drawings

PYRANIC DERIVATIVES USEFUL AS INTERMEDIATES IN MAKING MUSCONE

SUMMARY OF THE INVENTION

This is a division of application Ser. No. 183,722 filed Sept. 3, 1980 now U.S. Pat. No. 4,335,262.

This invention provides a process for the preparation of muscone, which process comprises treating a bicyclic compound of formula

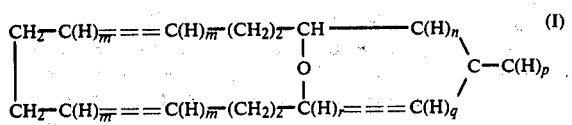

wherein the dotted lines stand for a single or a double bond, and wherein
 m stands for integer 1 or 2,
 $n=1$ and $p=3$ or $n=2$ and $p=2$, and
 $r=1$ and $q=2$ or $r=0$ and $q=1$,
 with hydrogen in an inert organic solvent and in the presence of noble metal catalyst.

The invention relates further to a pyranic derivative of formula

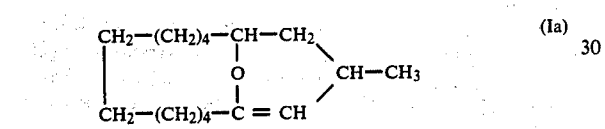

and to a process for its preparation which comprises subjecting a cyclic diol of formula

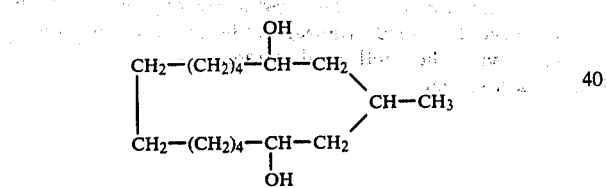

to dehydrogenation and dehydration.

A further object of the invention is a process for the preparation of unsaturated macrocyclic ketones of formula

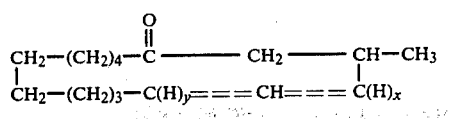

wherein the dotted lines stand for a single or a double bond, and wherein
 $x=1$ and $y=2$, or
 $x=2$ and $y=1$
which comprises treating a pyranic derivative of

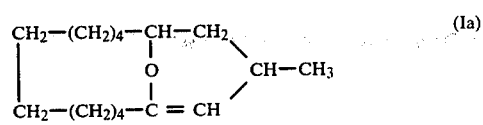

with an acidic agent in an inert organic medium.

BACKGROUND OF THE INVENTION

Among the most appreciated musky ingredients known in the art of perfumery, muscone, or 3-methylcyclopentadecaonone, has acquired a special renown. In spite of this, muscone has not found a widespread utilisation in the art for lack of economical synthetic processes for its preparation.

Among the variety of known processes, one may cite the following:

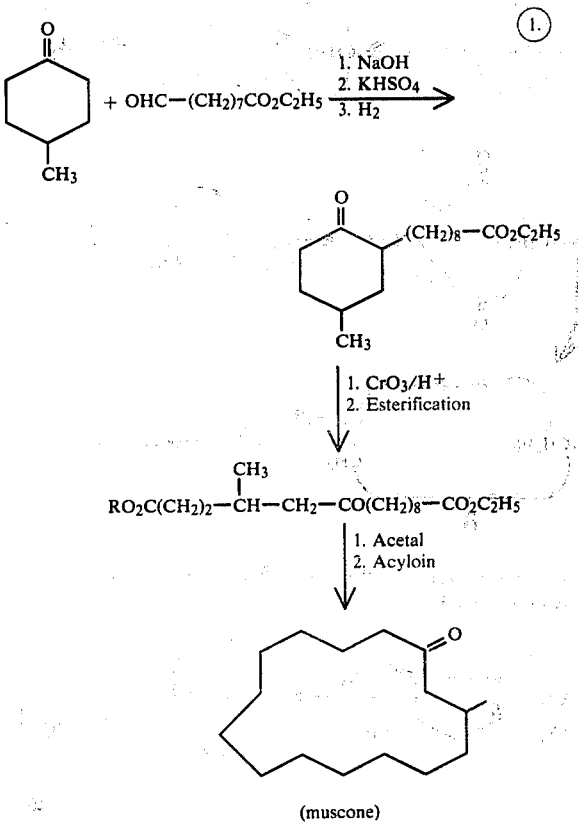

reference: J. Chem. Soc. 4154-7 (1964)

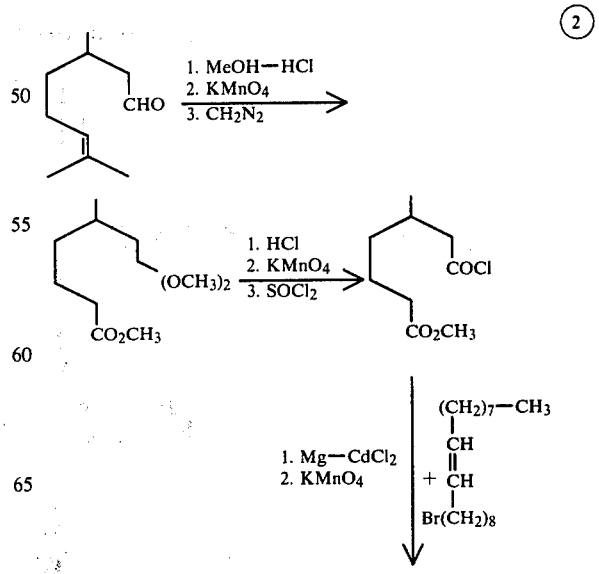

3

-continued

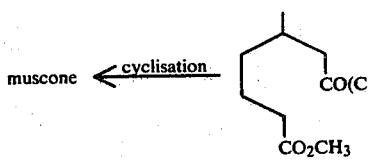

reference: Tetrahedron 20, 11, 2601 (1964)

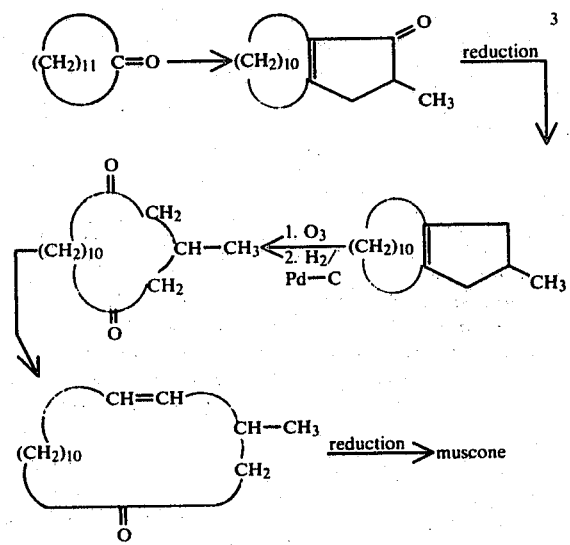

reference: Helv. Chim. Acta, 50, 705 (1967) or the following variant:

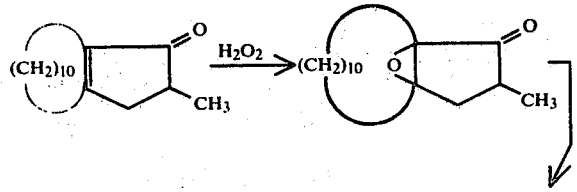

4

-continued

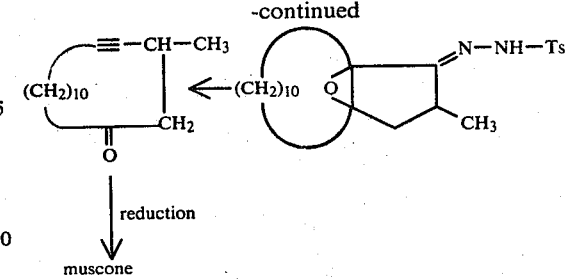

reference: Helv. Chim. Acta, 50, 708 (1967).

By making use of easily available starting materials, the processes of the instant invention which are characterized by a limited number of reaction steps represent new and original solutions to the industrial preparation of muscone.

PREFERRED EMBODIMENTS OF THE INVENTION

As indicated above a process for the preparation of muscone according to the invention consists in treating bicyclic compound (I) with hydrogen in the presence of noble metal catalysts. Suitable catalysts include platinum and palladium. Commercial 10% platinum on charcoal is perfectly adapted to promote the reaction in question.

The process is preferably carried out in an autoclave and the operation is conducted by exerting a slight pressure on the reactants kept under a hydrogen atmosphere. The details of the whole operation are given in the following examples.

The reaction is carried out in an inert organic solvent. Suitable solvents include in particular aliphatic hydrocarbons, petrol ether being preferred.

Bicyclic compounds (I), used as starting materials in the above described process, can be prepared in accordance with the method illustrated by the following reaction scheme:

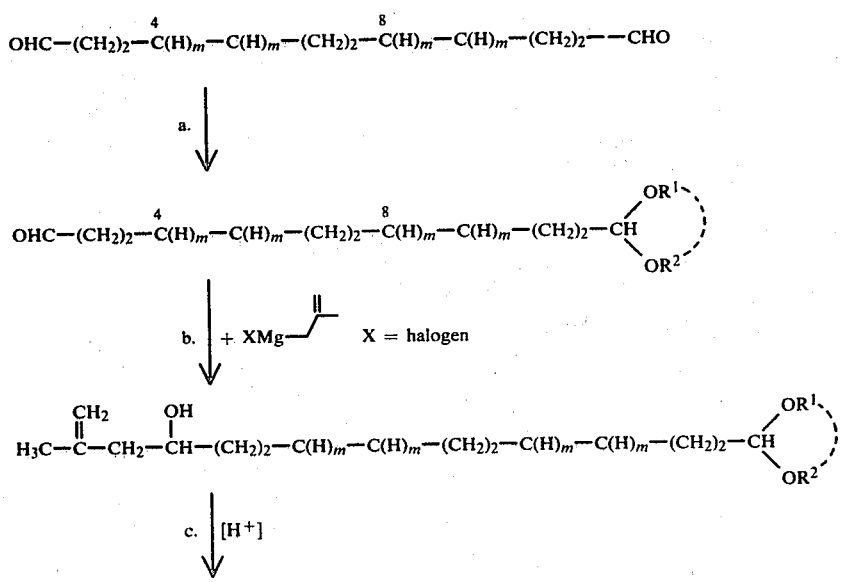

-continued $$CH_2-C(H)_m-C(H)_m-(CH_2)_2-CH-C(H)_n$$
$$\phantom{CH_2-C(H)_m-C(H)_m-(CH_2)_2-CH}O\phantom{xxx}C-C(H)_p$$
$$CH_2-C(H)_m-C(H)_m-(CH_2)_2-CH-CH_2$$

New compound of formula (Ia), one of the starting materials of the above described process of the invention, is obtained according to an original process which consists in dehydrogenating and dehydrating the cyclic diol of formula $$\phantom{xxxxxx}OH$$
$$CH_2-(CH_2)_4-CH-CH_2$$
$$\phantom{CH_2-(CH_2)_4-CH-CH_2}CH-CH_3$$
$$CH_2-(CH_2)_4-CH-CH_2$$
$$\phantom{xxxxxx}OH$$

Such an operation is effected in the presence of Raney copper at a temperature of between about 150° and about 200° C. As a result of it we could obtain desired compound (Ia) accompanied by traces of its isomeric derivative of formula $$CH_2-(CH_2)_4\phantom{xxx}CH-CH_2$$
$$\phantom{CH_2-(CH_2)_4xxx}O\phantom{xxx}CH-CH_3$$
$$CH_2-(CH_2)_3-CH=C\phantom{xx}CH_2$$

Whenever desired, the pure compound can be separated and purified by means of the usual techniques, such as e.g. vapor phase chromatography. However, the mixture as directly obtained by the disclosed process can be utilized directly without inconveniences for the preparation of muscone.

The enol-ether of formula (Ia) cannot only be used as intermediate for the preparation of muscone, but also as starting material for preparing muscenone, a compound of formula $$\phantom{xxxxxx}O$$
$$\phantom{xxxxxx}\|$$
$$CH_2-(CH_2)_4-C\phantom{xxx}CH_2\phantom{xxx}CH-CH_3$$
$$CH_2-(CH_2)_3-C(H)_y===CH===C(H)_x$$

wherein the dotted lines stand for a single or a double bond, and wherein
x=1 and y=2, or
x=2 and y=1.

This compound represents an interesting odorous ingredient as well as a useful intermediate in the synthesis of muscone [see DE-PS No. 16 68 054].

In accordance with the invention, muscenone is obtained by a process which consists in treating enolether (Ia) with an acidic agent in an inert organic medium. Preferentially, effective acidic agents are selected from the class of protonic mineral acids, acidic cationic resins and diatomaceous earths. For all practical purposes phosphoric acid is preferred. According to a preferred embodiment, the reaction is carried out by means of 80% aqueous phosphoric acid in admixture with an aromatic hydrocarbon solvent in a vessel equipped with a lateral distillation column; water was thus taken off azeotropically. Suitable aromatic hydrocarbons include benzene, toluene and xylene. Toluene is preferred.

The reaction temperature can vary in a wide range of values, for practical reasons however the reaction is effected at the boiling point of the chosen solvent.

The invention is better illustrated but not limited to the following examples wherein the temperatures are indicated in degrees centigrade.

EXAMPLE 1

Preparation of muscone 300 g of 16-oxa-3-methylbicyclo[10.3.1]pentadecane, 300 ml of petrol ether (b.p. 80°–100°) and 3 g of 10% platinum on charcoal have been introduced in a 1 l stainless steel autoclave. After closing, the autoclave was freed from air by three sequential injections of nitrogen, whereupon hydrogen was introduced twice at 3 bars. The pressure was decreased to 1 bar and the reactor was heated to 275°; in such a way, the resulting registered internal pressure increased to 30 bars and the stirring was started.

The course of the reaction was followed by gas phase chromatography, 6 to 10 hours were sufficient to complete the conversion into muscone.

After cooling, the reactor was freed from remaining hydrogen by sequential three injections of nitrogen and the mixture was filtered. Muscone was then obtained in 90% yield by subjecting the reaction mixture to usual working up.

16-oxa-3-methylbicyclo[10.3.1]pentadecane, used as starting material in the hereinabove described process can be prepared as follows:

1 g of 16-oxa-3-methylbicyclo[10.3.1]pentadeca-2,8,12-triene or of 16-oxa-3-methylbicyclo[10.3.1]pentadec-2-ene, in 50 ml ethanol, was perhydrogenated by subjecting the stirred alcoholic solution to the action of hydrogen at room temperature in the presence of 0.2 g of 10% palladium on charcoal.

The desired product was obtained in a ≧80% yield. The product was characterized by the following spectral data:

NMR: 0.9 (3H, d, J=7); 1.35 (13H, m); 3.1–3.6 (2H, m) δ ppm.

MS: M+ =238 (50); m/e: 223 (12), 194 (30), 112 (35), 99 (55), 81 (66), 69 (70), 55 (100), 41 (59).

EXAMPLE 2

Preparation of muscone 300 g of 16-oxa-3-methylbicyclo[10.3.1]pentadec-1-ene, 300 g of pentrol ether (b.p. 80°–100°) and 3 g of 10% platinum on charcoal have been introduced in a stainless steel autoclave of 1 l. The process is carried out as indicated in Example 1.

By carrying out the reaction of 1 h time, at a temperature of 20° and at 2–3 bars we have noticed a conversion into 16-oxa-3-methylbicyclo[10.3.1]pentadecane. The reaction temperature was increased to 275° which in turn brought the pressure to about 30 bars, and the mixture was treated as indicated in Example 1 to give muscone in 90% theoretical yield.

EXAMPLE 3

Preparation of muscone 5 g of 10% palladium on charcoal have been activated by refluxing it in 175 ml of xylene in a hydrogen atmosphere for 30 min. The flow of hydrogen was then adjusted at about 30–40 ml/min. and the temperature was kept at 135° and at that temperature 20 g of 16-oxa-3-methylbicyclo[10.3.1]pentadec-2-ene have been added thereto.

The course of the reaction was followed by usual vapor phase chromatography. The unsaturated tricyclic ether was thus converted into muscone in a 80% yield. The obtained product was accompanied by about 20% of 16-oxa-3-methylbicyclo[10.3.1]pentadecane.

EXAMPLE 4

Preparation of 16-oxa-3-methylbicyclo[10.3.1]pentadec-1-ene

A mixture of 150 g (0.58M) of 3-methyl-cyclopentadecan-1,5-diol and 75 g of Raney copper in 30% aqueous suspension was heated under reduced pressure. The temperature was increased up to 165° in 1–1½ h.

A strong release of hydrogen was observed at the beginning of the reaction. Temperature and pressure varied between 45 Torr (30°) and 20 Torr (165°).

At 165° a second fraction of 450 g (1.75M) of 3-methylcyclopentadecan-1,5-diol, melt at 80°, was added dropwise within 2–3 h. The reaction was endothermic. Once the addition was over, the reaction mixture was stirred during 2–3 supplementary hs. at 160°–165° and the pressure was decreased to about 2 Torr while the desired bicyclic ether was collected directly by distillation. 483.2 g were thus obtained at b.p. 150°/1 Torr (purity: 90%). The analytical characteristics of the product were the following:

IR: 1668 cm$^{-1}$.

NMR: 0.95 (3H, d, J=7); 1.3–1.5 (20H, m); 1.8–2.2 (3H, m); 3.8–4.1 (1H, m); 4.2–4.32 (1H, m) δ ppm.

MS: M$^+$=236 (45); m/e: 221 (40), 194 (20), 178 (20), 135 (35), 95 (75), 81 (60), 69 (100), 55 (90), 41 (90).

EXAMPLE 5

Preparation of muscenone (3-methyl-cyclopentadec-4-en-1-one)

236.3 g of 16-oxa-3-methylbicyclo[10.3.1]pentadec-1-ene and 34 g of 80% aqueous phosphoric acid in 1.9 l of toluene were heated to the boiling during 2½ h. The reactor was equipped with a lateral water separator device so that water could be gradually taken off during the reaction. After cooling, the reaction mixture was washed twice with water, then with 10% aqueous sodium carbonate and finally with water until neutrality.

By extraction of the mother liquors with toluene and working up of the combined organic extracts, there were obtained 218.2 g of muscenone having b.p. 115°–130°/0.2 Torr (purity about 95%); theoretical yield 87.5%.

What we claim is:

1. A pyranic derivative of formula

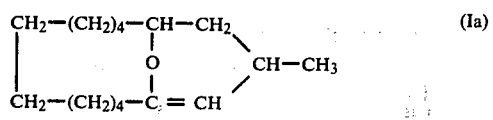

(Ia)

* * * * *